(12) United States Patent
Reichert et al.

(10) Patent No.: US 7,537,734 B2
(45) Date of Patent: May 26, 2009

(54) INTEGRATED OPTIC WAVEGUIDE IMMUNOSENSOR

(75) Inventors: W. Monty Reichert, Durham, NC (US); James N. Herron, Salt Lake City, UT (US); Douglas A. Christensen, Salt Lake City, UT (US); Hsu-Kun Wang, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 74 days.

(21) Appl. No.: 09/973,557

(22) Filed: Oct. 10, 2001

(65) Prior Publication Data
US 2002/0034457 A1 Mar. 21, 2002

Related U.S. Application Data

(60) Division of application No. 09/412,731, filed on Oct. 5, 1999, now Pat. No. 6,350,413, which is a continuation of application No. 08/961,827, filed on Oct. 31, 1997, now Pat. No. 5,961,924, which is a continuation of application No. 08/393,450, filed on Feb. 23, 1995, now Pat. No. 5,814,565.

(51) Int. Cl.
*G01N 21/00* (2006.01)
*G01N 33/53* (2006.01)
*G01N 33/552* (2006.01)
*G01N 21/55* (2006.01)
*G01N 21/41* (2006.01)
*G02B 6/00* (2006.01)

(52) U.S. Cl. ............... 422/82.11; 435/7.9; 436/518; 356/445; 356/12; 356/128

(58) Field of Classification Search ............... 422/82.11, 422/82.05, 82.07, 82.01, 67, 102; 250/458.1, 250/459.1; 385/12; 436/527, 172, 165, 518; 702/22, 28, 30, 32; 435/7.9; 356/445, 12, 356/128
See application file for complete search history.

(56) References Cited

U.S. PATENT DOCUMENTS 3,449,037 A * 6/1969 Koester ............... 385/116

(Continued)

FOREIGN PATENT DOCUMENTS

EP 0184600 * 6/1986

(Continued)

OTHER PUBLICATIONS

*Applied Spectroscopy 42*: 68-72, J.T. Ives and W.M. Reichert, 1988.

(Continued)

*Primary Examiner*—Jill Warden
*Assistant Examiner*—Lore Ramillano
(74) *Attorney, Agent, or Firm*—Ballard Spahr Andrews & Ingersoll, LLP (57) ABSTRACT

A composite waveguide for evanescent sensing in fluorescent binding assays comprising a substrate layer having one or more thin-film waveguide channels deposited thereon. Binding molecules having the property of binding with specificity to an analyte are immobilized on the surface of the thin-film channels. In preferred embodiments, the composite waveguide includes integral light input coupling means adapted to the thin-film channels. Light coupling means may include a grating etched into the substrate prior to deposition of the thin film, or a waveguide coupler affixed to the upper surface of the thin film. The waveguide coupler has an input waveguide of high refractive index which receives the laser light through one end, propagating it by total internal reflection. Propagated light is coupled evanescently into the thin film across a spacer layer of precise thickness with a lower index of refraction than that of the input waveguide or the thin-film waveguide.

65 Claims, 5 Drawing Sheets

U.S. PATENT DOCUMENTS

| | | | |
|---|---|---|---|
| 3,934,061 A | | 1/1976 | Keck et al. |
| 3,939,350 A | | 2/1976 | Kronick et al. |
| 4,166,105 A | | 8/1979 | Hirschfeld |
| 4,264,766 A | | 4/1981 | Fischer |
| 4,399,099 A | * | 8/1983 | Buckles ..................... 422/58 |
| 4,608,344 A | * | 8/1986 | Carter et al. ................. 436/34 |
| 4,775,637 A | | 10/1988 | Sutherland et al. |
| 4,815,843 A | | 3/1989 | Tiefenthaler et al. |
| 4,849,340 A | | 7/1989 | Oberhardt |
| 4,857,273 A | | 8/1989 | Stewart |
| RE33,064 E | | 9/1989 | Carter |
| 4,880,752 A | | 11/1989 | Keck |
| 4,909,990 A | | 3/1990 | Block et al. |
| 5,006,333 A | | 4/1991 | Seifer et al. |
| 5,006,716 A | | 4/1991 | Hall |
| 5,043,278 A | | 8/1991 | Nagaoka et al. |
| 5,071,248 A | | 12/1991 | Tiefenthaler et al. |
| 5,081,012 A | | 1/1992 | Flanagan |
| 5,120,131 A | * | 6/1992 | Lukosz ..................... 356/481 |
| 5,166,515 A | * | 11/1992 | Attridge ............... 250/227.25 |
| 5,192,502 A | | 3/1993 | Attridge |
| RE34,394 E | | 9/1993 | Bunting |
| 5,248,620 A | | 9/1993 | Sluka et al. |
| 5,340,715 A | * | 8/1994 | Slovacek et al. ............... 435/6 |
| 5,344,784 A | * | 9/1994 | Attridge ..................... 436/518 |
| 5,512,492 A | * | 4/1996 | Herron et al. ............... 436/518 |
| 5,577,137 A | * | 11/1996 | Groger et al. .................. 385/12 |
| 5,589,136 A | | 12/1996 | Northrup et al. |
| 5,677,196 A | | 10/1997 | Herron et al. |
| 5,814,565 A | | 9/1998 | Reichert et al. |
| 5,822,472 A | | 10/1998 | Danielzik et al. |
| 5,832,165 A | * | 11/1998 | Reichert et al. ............. 385/130 |
| 5,846,708 A | | 12/1998 | Hollis et al. |
| 5,846,842 A | | 12/1998 | Herron et al. |
| 5,959,292 A | | 9/1999 | Duveneck et al. |
| 6,340,598 B1 | | 1/2002 | Herron et al. |
| 6,350,413 B1 | | 2/2002 | Reichert et al. |

FOREIGN PATENT DOCUMENTS

| | | |
|---|---|---|
| EP | 0 517 516 | 9/1992 |
| EP | 0 519 623 A2 | 12/1992 |
| GB | 2220083 | 12/1989 |
| WO | WO 88/10418 | 12/1988 |
| WO | 9001166 | 2/1990 |
| WO | WO 90/05295 | 5/1990 |
| WO | 9006503 | 6/1990 |
| WO | WO 91/10122 | 7/1991 |
| WO | 9113339 | 9/1991 |
| WO | WO 94/27137 | 11/1994 |
| WO | WO 95/03538 | 2/1995 |
| WO | WO 99/38787 | 7/1999 |

OTHER PUBLICATIONS

"Total internal reflection fluorescence surface sensors", Ives, Reichert, Lin, Hlady, Reinecke, Suci, VanWagenen, Newby, Herron, Dryden and Andrade, *Optical Fiber Sensors*, pp. 391-396, eds. A.N. Chester et al., 1987 (M. Nijhoff, publ.).

"Integrated optical waveguide attenuated total reflection spectrometry and resonance Raman spectroscopy of adsorbed cytochrome c", D.S. Walker, H.W. Hellings, S.S. Saavedra, and W.M. Reichert, *J. Phys. Chem. 97*: 10217-10222 (1993).

"Corning 7059, silicon oxynitride, and silicon dioxide thin-film integrated optical waveguides: in search of low loss, nonflourescent, reusable glass waveguides", D.S. Walker, W.M. Reichert, and C.J. Berry, *Applied Spectroscopy 46*: 1437-1441 (1992).

Lee, Jin Ho; Kopecek, J. and Andrade, J.D., "Protein-resistant surfaces prepared by PEO-containing block copolymer surfactants", Journal of Biomedical Materials Research, Published by John Wiley & Sons, p. 351-368 (1989).

Carlsson, J.; Drevin, K. and Axen, R., Protein Thiolation and Reversible Protein-Protein Conjugation, Biochem J. (1978) 173, 723-737, Printed in Great Britain.

Choquette, Steven J., et al., "Planar Waveguide Immunosensor with Fluorescent Liposome Amplification," *Analytical Chemistry*, 64(1):55-60, Jan. 1, 1992.

Fattinger, Ch., et al., "The Difference Interferometer: A Highly Sensitive Optical Probe for Quantification of Molecular Surface Concentration," *Biosensors & Bioelectronics*, 8:99-107, 1993.

Ho, Z.Z., et al., "Large Area Waveguide Sensor for Multiple Analytes Detection," *SPIE*, 2136:344-351, 1994.

Huber, W., et al., "Direct Optical Immunosensing (Sensitivity and Selectivity)," *Sensors and Actuators*, B.6:122-126, 1992.

Discovery Technologies AG, Third-Party Observation, Aug. 25, 1999.

D.K.W. Lam, "Low temperature plasma chemical vapor deposition of silicon oxynitride thin-film waveguides", *Applied Optics*, 23(16):2744-46, Aug. 15, 1984.

Supplementary European Search Report dated Feb. 12, 1999 (2 pages).

Zhou et al., "Multichannel Evanescent Fluorescence Immunosensing Using Potassium and Sodium Ion-Exchanged Patterned Waveguides," Journal of Molecular Electronics, vol. 7 (Jul. 1991), pp. 135-149.

Herron et al., "Fluorescent Immunosensors Using Planar Waveguides," SPIE vol. 1885, Advances in Fluorescence Sensing Technology (1993), pp. 28-39.

Dierker et al., "Random-Field Transition of a Binary Liquid in a Porous Medium," The American Physical Society, vol. 58, No. 18 (May 4, 1987), pp. 1865-1868.

Dierker et al., "Dynamics of Thin Tilted Hexatic Liquid Crystal Films," The American Physical Society, vol. 59, No. 9 (Aug. 31, 1987), pp. 1002-1005.

Sloper et al., "A Planar Indium Phosphate Monomode Waveguide Evanescent Field Immunosensor," Sensors and Actuators, vol. B1, Elsevier Sequoia, The Netherlands (1990), pp. 589-591.

Zhou et al., "An Evanescent Fluorescence Biosensor Using Ion-Exchanged Buried Waveguides and the Enhancement of Peak Fluorescence," Biosensors & Bioelectronics, vol. 6, Elsevier Science Publishers Ltd. (1991), pp. 595-607.

* cited by examiner

INTEGRATED OPTIC WAVEGUIDE IMMUNOSENSOR

CROSS REFERENCE TO RELATED APPLICATIONS

This application is a divisional of application Ser. No. 09/412,731, filed Oct. 5, 1999 now U.S. Pat. No. 6,350,413, pending, which is a continuation of application Ser. No. 08/961,827, filed Oct. 31, 1997, now U.S. Pat. No. 5,961,924, issued Oct. 5, 1999, which is a continuation of application Ser. No. 08/393,450, filed on Feb. 23, 1995, now U.S. Pat. No. 5,814,565, issued Sep. 29, 1998.

TECHNICAL FIELD

The invention relates to apparatus for solid-state biochemical binding assays, and especially to optical structures utilizing evanescent sensing principles for use in such apparatus and assays.

BACKGROUND

Immunoassays exploiting the properties of an optical technique known as total internal reflection (abbreviated "TIR") are proving to be a valuable tool for detection of analytes at concentrations of $10^{-10}$ to $10^{-13}$ molar or below, without a wash step. When a light beam traveling in a waveguide is totally internally reflected at the interface between the waveguide and an adjacent medium having a lower refractive index, a portion of the electromagnetic field of the TIR light penetrates shallowly into the adjacent medium. This phenomenon is termed an "evanescent penetration" or "evanescent light". The intensity of evanescent light drops off exponentially with distance from the waveguide surface.

Binding assays, in general, are based on the strong affinity of a selected "capture" molecule to specifically bind a desired analyte. The capture molecule/analyte pair can be an antibody/antigen pair or its converse, a receptor/ligand pair or its converse, etc., as known in the art. In a fluorescent binding assay, the binding of the analyte to the antibody is monitored by a tracer molecule which emits fluorescent light in response to excitation by an input light beam.

One of several possible schemes for exploiting the properties of evanescent light fields for fluorescence measurements is as follows. If an antibody is immobilized on an optical structure in which a light beam is being propagated by TIR, the resulting evanescent light can be used to selectively excite tracer molecules that are bound (whether directly or indirectly) to the immobilized antibody. Tracer molecules free in solution beyond the evanescent penetration depth are not excited and, therefore, do not emit fluorescence. For silica-based optical materials or optical plastics such as polystyrene, with the adjacent medium being an aqueous solution, the evanescent penetration depth is generally about 1000 to 2000 Å (angstroms). The amount of fluorescence is thus a measure of the amount of tracer bound to the immobilized capture molecules. The amount of bound tracer in turn depends on the amount of analyte present, in a manner determined by the specifics of the immunoassay procedure.

U.S. Pat. Nos. RE 33,064 to Carter, 5,081,012 to Flanagan et al., 4,880,752 to Keck, 5,166,515 to Attridge, and 5,156,976 to Slovacek and Love, and EP publication Nos. 0 517 516 and 0 519 623, both by Slovacek et al., all disclose apparatus for immunoassays utilizing evanescent sensing principles.

Desirably, an immunosensor should be capable of accurately and repeatably detecting analyte molecules at concentrations of $10^{-13}$ M (molar) to $10^{-15}$ M and preferably below. At present, such sensitivity is not believed to be available in a commercially practical and affordable immunosensor. Also desirably, an immunosensor should provide multiple "channels", that is, the capacity for measuring multiple analytes and multiple measurements of the same analyte, on the same waveguide substrate. Such an immunosensor would allow both self-calibration with known standards and screening for a panel of different analytes selected for a particular differential diagnostic procedure.

One approach to improving the sensitivity (lowering the detection limits) of fluorescent immunosensors, proposed by Ives et al. (Ives, J. T.; Reichert, W. M.; Lin, J. N.; Hlady, V.; Reinecke, D.; Suci, P. A.; Van Wagenen, R. A.; Newby, K.; Herron, J.; Dryden, P. and Andrade, J. D. "Total Internal Reflection Fluorescence Surface Sensors" in A. N. Chester, S. Martellucci and A. M. Verga Scheggi Eds., *Optical Fiber Sensors*, NATO ASI Series E, Vol. 132, 391-397, 1987), is to use waveguides which are very thin, perhaps about 1 mm in thickness. Such thin waveguides may provide higher evanescent intensity and a reflection density of 500-1000 reflections/cm or more. However, the potential lowering of the detection limit by use of thin-film waveguides is achievable only if the waveguide material is nonfluorescent and low-loss. Most present evanescent immunosensing technology ("thick" waveguides) utilizes silica glass ($SiO_2$), which is intrinsically nonfluorescent. Only the purest grades of silica, for example, UV grade quartz which is rather expensive, lack the additives and impurities that fluoresce (Dierker et al., 1987).

Further, one cannot simply fabricate silica-on-silica waveguides by depositing $SiO_2$ onto a quartz substrate because there would be no refractive index difference. Instead, one must either (1) fabricate a glass waveguide of higher refractive index than the underlying silica substrate, or (2) deposit a silica waveguide onto a transparent substrate of a lower refractive index. Therefore, other materials must be employed.

Thin film waveguides have been described by Sloper et al. ("A planar indium phosphate monomode waveguide evanescent field immunosensor," *Sensors and Actuators*, B1: 589-591, 1990) and Zhou et al. ("An evanescent fluorescence biosensor using ion-exchanged buried waveguides and the enhancement of peak fluorescence", *Biosensors and Bioelectronics*, 6:595-607, 1991. However, neither of these devices was capable of achieving detection of analyte concentrations significantly below $10^{-10}$ molar. The waveguide structure of Sloper et al. was of the gradient-index type, formed by diffusion of a dopant into the silica base, which results in a drop-off of dopant concentration with distance from the interface. The waveguide of Zhou et al. had only a single "channel" (measurement region).

Therefore, a need exists for an optical structure useful in an evanescent sensing immunoassay which provides increased levels of propagated TIR light and increased evanescent field intensity, as well as multiple measurement regions. Such an optical structure should desirably be capable of detection of analyte concentrations of $10^{-13}$ M and preferably below $10^{-15}$ M. A need also remains for an immunosensor including such an optical structure which is sufficiently inexpensive and practical to produce as a commercial device, and which provides accurate and repeatable results in the hands of non-skilled persons. Still further, a need also remains for a biosensor capable of detecting ions, as opposed to hormones or other biological molecules.

SUMMARY OF THE INVENTION

The invention comprises a step gradient waveguide, also described as a composite waveguide, useful for performing evanescent sensing assays. The waveguide includes a thick substrate formed of a first optical material of refractive index $n_1$ and having a first surface, and a thin film formed of a second optical material having a refractive index $n_2$ which is greater than $n_1$, the thin film being disposed adjacent and in operative contact with the substrate. The optical substrate has a thickness which may be from about 0.3 µm up to 10 mm or more, depending on the material used, while the thin film has a thickness which is generally between about 0.3 µm and about 5 µm. Highly preferably, the waveguide thickness is selected to provide for internal propagation in from one to four modes only.

The invention further encompasses a kit comprising the composite waveguide and at least one specific binding molecule immobilized to the thin film and constructed to bind with specificity an analyte. The kit may be further constructed for use in either a competition assay or a sandwich-type assay. The tracer molecule is further constructed to be excited by evanescent light penetrating from the thin film into an adjacent aqueous environment and to respond thereto by emitting a photodetectable tracer signal.

In a preferred embodiment, the composite waveguide comprises the substrate with a plurality of thin strips of the thin film disposed in parallel array thereon, and the kit further includes a second solution containing a known concentration of analyte in a buffer.

In preferred embodiments of the composite waveguide, coupling means are integrally adapted and in operative contact with the thin film for coupling input light thereinto. One embodiment of coupling means is a grating etched into the substrate on the surface adjacent the thin film. Alternatively, instead of a physical grating, a grating-type coupler may be composed of an array of segments of a different refractive index $n_5$ disposed in the substrate in a regular spacing analogous to that of the ridges in a grating. In another alternate embodiment, a relatively thick waveguide coupler is disposed on the planar surface of the thin-film waveguide opposite the substrate, near one end of the composite waveguide. The waveguide coupler is dimensioned and constructed of appropriate optical material so as to evanescently couple light propagated by TIR in a thick input waveguide across a thin spacing layer into the thin-film waveguide.

In a highly preferred embodiment, the composite waveguide is constructed by vapor deposition of the thin film on the substrate, masking of the thin strips with a resist compound, and etching the thin film to expose the substrate in the unmasked areas. The resist compound is then removed to allow immobilization of the binding molecules to the thin strips.

The invention further embraces apparatus for performing specific binding assays, the apparatus comprising a composite waveguide together with an optical unit having a light source positioned to direct light into the waveguide for propagation by total internal reflectance therein, and detection means oriented to detect light from a region proximal to the optical structure.

The integrated optic waveguide ("IOW") of the invention is capable of detecting analyte concentrations in the femtomolar ($10^{-18}$ M) range. Such sensitivity is well beyond that achieved by other thin-film evanescent sensors, and also beyond the sensitivity expected solely on the basis of the increased reflection density intensity in the thin-film waveguide.

BRIEF DESCRIPTION OF THE DRAWINGS

In the drawings, which depict the best mode presently known for carrying out the invention.

DETAILED DESCRIPTION OF THE ILLUSTRATED EMBODIMENTS

Figure 1A:
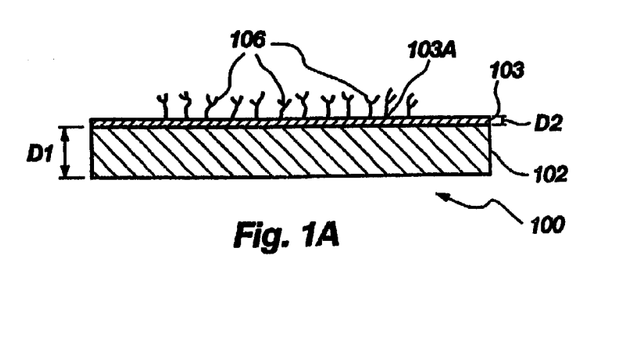
FIG. 1A is a side cross-sectional view of the composite waveguide of the invention.

A composite waveguide indicated at 100 has a substrate 102 formed of a first optical material of refractive index $n_1$ (FIG. 1A) and a thin-film waveguide layer 103 of a second optical material of refractive index $n_2$, with $n_2$ being greater than $n_1$. The waveguide layer 103 has a plurality of binding molecules 106, each constructed to specifically bind an analyte, immobilized on the upper surface 103A. The substrate 102 has a thickness D1 which may be from about 0.3 µm up to 10 millimeters (mm) or more, while the thin-waveguide layer 103 has a thickness D2 of between about 0.3 microns (µm) and 5 µm. If the substrate 102 is relatively thick, perhaps 0.5 mm or more, as shown in FIG. 1A, it may also serve as a mechanical support in addition to having the optical properties necessary for supporting effective waveguiding of light in the thin-film waveguide layer 103. However, in some embodiments it is preferred, generally for easier manufacture, that the substrate 102 be comparatively thin. In such cases, an additional support layer (not shown) may be added below the optical substrate 102 (not shown).

In a presently preferred embodiment, the substrate 102 is silicon dioxide, either in the form of a $SiO_2$ thin film laid down by vapor deposition or other techniques as known in the art, or in the form of quartz (here defined as including both natural quartz and fused silica or other manmade quartz), with a waveguide layer formed of silicon oxynitride ($Si_zO_xN_y$ or, generally, "SiON"). The term "deposited $SiO_2$" is used hereinafter to distinguish the deposited $SiO_2$ from quartz/fused silica, etc. Silicon dioxide has a refractive index of n=1.47 and, if sufficiently pure, exhibits very low fluorescence. Silicon oxynitride is mechanically durable, transparent in the visible wavelength range, substantially nonfluorescent, and has a refractive index generally above 1.5 and reaching as high as 2.0, depending on the stoichiometric ratios of 0 to N. In a further presently preferred embodiment, the SiON is $Si_2O_3N$.

In another embodiment, the substrate 102 is formed of SiON having a refractive index $n_1$ and the waveguide film 103 is formed of SiON having a refractive index $n_2 > n_1$. The refractive index of the SiON compositions is controlled by the proportion of nitrogen. That is, the SiON of the substrate will have a lower proportion of nitrogen than the SiON of the waveguide film.

In still another embodiment, the substrate 102 is formed of $MgF_2$ (magnesium fluoride) having refractive index $n=1.38$ and the waveguide layer 103 is a pure silicon dioxide thin film. Because the MgF substrate is formed by vapor deposition techniques or the like, which are tedious and comparatively expensive, in this embodiment, the substrate 102 need be only sufficiently thick to ensure efficient propagation of at least one guided mode. At present, the SiON waveguide layer 103 is preferred, as it provides better adherence to the substrate in aqueous solutions than the $MgF_2$ waveguide. However, the $MgF_2$ waveguide/$SiO_2$ composite waveguide may be entirely suitable for use with nonaqueous solvents.

In a presently preferred embodiment of a structure including a thin-film SiON waveguide, the substrate 102 is a layer of $SiO_2$ deposited on a silicon wafer support. This is preferred because the surface of the substrate 102 is much more uniform and smooth, which in turn produces a much smoother, planar surface in the deposited SiON film. The increased smoothness of the waveguide surfaces reduces the propagation losses by at least two-fold in comparison with a thin-film waveguide deposited on a quartz or fused silica substrate.

Figure 1B:
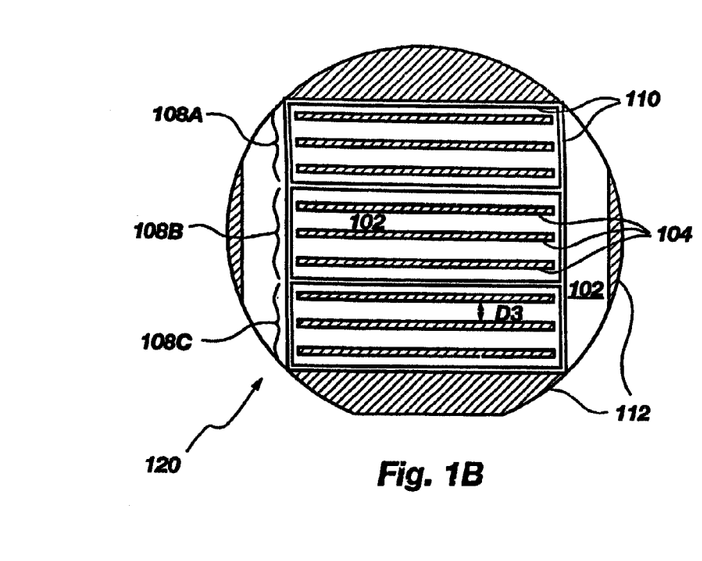
FIG. 1B is a top view of a composite waveguide module having a cross-sectional composition according to FIG. 1A.

In FIG. 1B, the waveguide layer is shown as a plurality of strips 104 which do not extend the full length of the substrate 102. This is an optional configuration of the waveguide layer designed to provide multiple waveguide "channels" for different sample solutions and/or for having different immobilized capture molecules. Further optionally, the composite waveguide 120 may be configured as a plurality of rectangular wells 108A, 108B, 108C, each containing three strips 104. The strips 104 are separated from one another by a distance D3 of at least about 5 mm. The wells 108A,B,C are separated by walls 110 extending upward from the substrate 102. The device of FIG. 1B may be formed by vapor deposition of the SiON over the entire surface of the substrate 102, masking the regions corresponding to the thin strips 104 with a resist compound, etching the exposed SiON to remove it from the substrate 102, and removing the resist compound. In FIG. 1B, shaded regions 112 represent areas of the waveguide which were not exposed to etchant. The binding molecules 106 are then immobilized to the thin strips 104. This can be accomplished by means known in the art of binding assays. Alternatively, the wells 108A, 108B, 108C may be configured for flow-cell type operation, as separate flow-through compartments for background, calibration (known analyte concentration), and test sample (unknown) solutions.

High-quality composite waveguides made of the material combinations described above can be formed using plasma-enhanced chemical vapor deposition (PECVD) to deposit a thin film over an entire surface of the substrate, and then lithographically etching away the thin film except in the desired strips. In the case of SiON, the PECVD is performed with a mixture of nitrogen, nitrous oxide, ammonia and silane gases, and the stoichiometry of $Si_zO_xN_y$ is varied by changing the respective partial pressures of the above components.

For the lithographic steps, it is presently preferred to use a reactive-ion etch (RIE) process with commercially available photoresist compounds. The areas of the film which are to become the strips or channels are coated with the resist, and the surrounding areas are etched down to the substrate. In the present embodiment, the DUV negative-tone photoresist XP89131 available from Shipley Co. is preferred, and the etchant is a plasma of $O_2$ and $CHCl_3$ gases. Positive tone resists such as XP2198 (Shipley Co.), APEX-E from IBM, and CAMP6 from OCG are also suitable (All of these compositions are proprietary). All of these resist compounds are of the chemical amplification type, comprised substantially of phenolic polymers. While older photoresists such as PMMA (polymethylmethacrylate) could be used, the chemically amplified DUV resists are considered to produce superior results for the present purposes.

Almost any other etching technique could be readily applied for etching the channels into the waveguide film, including plasma etch, ion milling, or a wet etch. However, where it is desired to use a substrate-etched grating to increase the coupling efficiency (see FIG. 2A and related description), the RIE process is preferred. This is because the etching process is critical to production of a highly anisotropic grating. RUE etching is believed to provide the best results for the grating, and wet etching would be unsuitable. For waveguides having an etched grating coupler, then it is convenient to use the RIE process to etch the channels as well.

It is also within contemplation that the thin-film waveguide channels could be produced by a wet lift-off process. In this process, the substrate of the waveguide would be masked to leave the channel regions bare, and the SiON thin film would then be deposited over the whole surface including the masking agent. After deposition of the film, the entire surface would be immersed in a solvent selected to "lift-off" or remove the mask, together with the waveguide film deposited on the mask, while leaving the film deposited on the bare quartz.

All steps of the waveguide fabrication should be performed in an extremely clean environment, preferably a clean-room meeting the standards of at least class 10.

Example 1

SiON Composite Waveguide Fabrication

Waveguides comprising a 1 μm thick film of $Si_2O_3N$ on $SiO_2$ have been produced as follows. A heated sample holder containing a 4 inch quartz wafer was placed in a plasma-enhanced chemical vapor deposition (PECVD) reactor. Process gasses flowed from the perimeter of the PECVD vessel, over the sample, and were then pumped out of the vessel through a central port. During deposition, the PECVD reactor was maintained at 300° C. and 1.25 Torr, with 50W of power to a 13.56 MHZ generator. The gas mixture consisted essentially of 27 standard $cm^3$ per minute (sccm) silane ($SiH_4$), 500 sccm nitrogen, 200 sccm ammonia, and 1300 sccm nitrous oxide. The respective inlet partial pressures were approximately 17 mTorr, 308 mTorr, 123 mTorr, and 802 mTorr. Under these conditions, the deposition rate was about 590 Å/minute and a 1 μm film was produced in about 15 minutes. These silicon oxynitride films had an approximate elemental ratio of Si:O:N=2:3:1 and a refractive index of about $n=1.53$ to 1.54.

Next, the $Si_2O_3N$ films were coated with photoresist, masked, and developed to expose all but nine parallel 1 mm×65 mm strips of the SiON film separated by 5 mm. The unmasked SiON was etched down to the quartz wafer. The photoresist was stripped, and the etched wafer was cleaved to produce three 23 mm×69 mm rectangular pieces, where each piece contained three parallel 1 μm thick channel waveguides. Only the two outside channels were used in the assays described here.

There are several properties of composite waveguides which can be correlated to their relative suitability for evanescent-sensing biochemical binding assays. These include the ability to withstand the solvent used in the assay, which is generally but not always water; the amount of propagated light lost per unit distance traveled in the waveguide ("propagation loss", expressed as dB per cm); the intrinsic level of fluorescence of the waveguide upon irradiation with light of the excitation wavelength to be used, as measured within the bandwidth of the tracer fluorescence emission; reflections/cm at the waveguide-superstrate interface ($N_r$); and adequate depth of evanescent penetration ($d_p$).

Example 2

Characterization of SiON Waveguide

Scanning electron microscopy was used to examine the shape and thickness of etched channel waveguides. A nominal channel should have optically smooth, rectangular edges and a uniform thickness. For optical characterization of channel waveguides, the beam of the 632.8 nm line from a HeNe laser was coupled into the waveguide using a prism coupler. In a typical experiment, values were determined for waveguide thickness ($t_{wg}$), refractive index ($n_{wg}$), internal reflection angle ($q_{wg}$), reflections/cm at the waveguide-superstrate interface ($N_r$) depth of penetration ($d_p$), and propagation loss (dB/cm). The data of Table 1 summarize the properties measured for a typical SiON waveguide constructed by the procedure outlined

TABLE I

Optical characterization of SiON waveguides

| waveguide parameter | air superstrate | water superstrate |
|---|---|---|
| $t_{wg}$ (μm) | 1.31 ± 0.11 | N.A. |
| $n_{wg}$ | 1.53 ± 0.0 | N.A. |
| propagation loss (dB/cm) | 0.76 ± 0.09 | N.D. |
| $q_{wg}$ (degrees) | 82.67 ± 0.47 | 82.85 ± 0.42 |
| $d_p$ (nm) | 44.10 ± 0.06 | 68.79 ± 0.29 |
| $N_r$ (reflections/cm) | 492.10 ± 71 | 479 ± 0.29 |

Each parameter was measured for three different channel waveguides with air as the superstrate. The mean and standard error of these measurements is reported. In addition, the last three parameters ($q_{wg}$, $d_p$, N) were determined when water was substituted for air as the superstrate. N.D.—not determined.

in Example 1. Also, these waveguides possess a high degree of physical definition and the desirable features of low propagation loss and minimal intrinsic waveguide fluorescence.

Example 3

Fabrication of $MgF_2$/$SiO_2$ Composite Waveguide

The $SiO_2$/$MgF_2$ laminates were deposited in situ by electron beam evaporation, using a multipocket electron beam gun in a Balzers BAK760 high-vacuum coater. The deposition chamber was evacuated to 2 μTorr, and the silica chips used as mechanical supports on which the laminates were deposited were heated to 200° C. The chamber pressure rose to 3.8 μTorr as a result of heating of the silica chips prior to deposition. The source materials, 99.9% pure $MgF_2$ and 99.999% pure $SiO_2$, were placed in molybdenum- and graphite-lined hearths, respectively, in the rotatable source carousel. Both source materials were brought to the deposition temperature with the shutter closed. First the $MgF_2$ was evaporated with a slowly sweeping 10-kV (kilovolt) electron beam (≈12 mm² elliptical spot size) followed by similar evaporation of the $SiO_2$. The deposition rates of $MgF_2$ and $SiO_2$ were controlled at 20 Å/s and 10 Å/s (angstroms per second), respectively, by means of an oscillating crystal monitor. A 0.36 μm film of $MgF_2$ was deposited in 3 minutes, and a 1.0 μm film of $SiO_2$ was deposited in 16 minutes.

Following construction of the physical portion of the waveguide, a plurality of specific binding molecules, that is, molecules having the property of specifically binding a chosen analyte, is immobilized on the surface of the thin-film waveguide channel(s). Such specific-binding molecules may be antibodies, receptor molecules, and the like, or fragments thereof that are operative to specifically bind the corresponding analyte. Converse pairs, e.g., such as an antigen for detecting certain antibodies with the analyte being the antibody, are also suitable. Other types of binding molecule/analyte pairs will be apparent to those of ordinary skill, as will means for immobilizing the binding molecule. Presently preferred means for immobilizing the binding molecule are discussed subsequently herein.

Figure 4A:
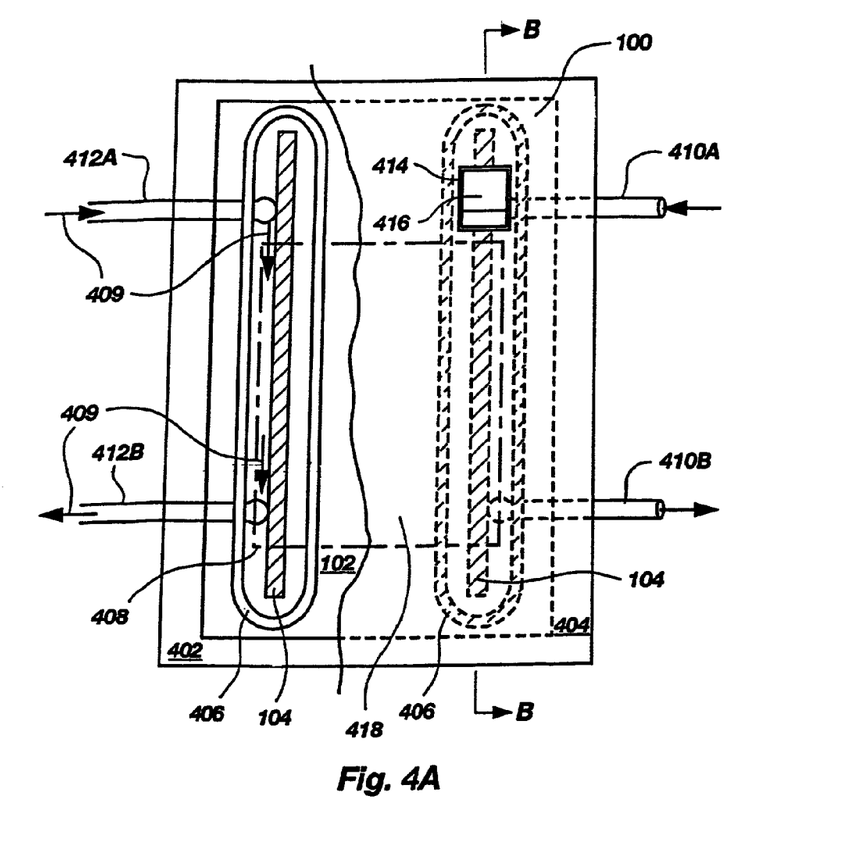
FIG. 4A is a schematic diagram of a top view with partial cutaway of a flow cell incorporating a multichannel composite waveguide.
Figure 4B:
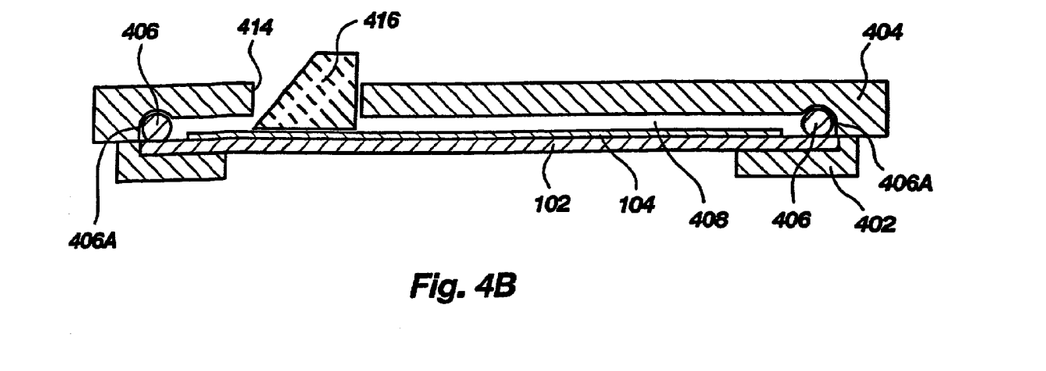
FIG. 4B is a side cross-section taken along line B-B of FIG. 4A.

A flow cell incorporating a two-channel waveguide fabricated and characterized as in Examples 1 and 2 is shown in FIGS. 4A and 4B. A composite waveguide 100 is held between a bottom plate 402 and a top plate 404 spaced by a pair of black silicone rubber o-ring gaskets 406 (FIG. 4B). Each gasket 406 is seated in a corresponding groove 406A milled in the top plate 404, and forms a longitudinal flow channel 408. The flow channels 408 have respective inlet ports 410A, 412A and outlet ports 410B, 412B. Arrows 409 indicate the direction of flow of liquid through the channel 408. Each flow channel 408 also has a hole 414 for placing a coupling prism 416. The interior of the bottom plate 402 has a window 418 milled therein to support the waveguide and provide a clear view of the waveguide bottom through the silica chip support layer. The aluminum parts of the entire flow cell are desirably flat black, to absorb stray light. Coupling prisms 416 (4 mm wide by 10 mm high truncated 45-45-90 LaSF prisms, $n_p$=1.83, obtained from Karl Lambrecht Co.) were fixed in place inside the windows 418 with GTE 118 RTV silicone rubber cement. A series of finger screws (not shown) were used to clamp the top and bottom plates 404, 402 to the substrate 102 and to maintain coupling pressure on the coupling prisms 416. Polyethylene screw-in tubing connectors, TEFLON® microtubing, and disposable syringes served as the sample delivery system (not shown). The sample volume of each channel 408 was 300 μL.

Prism coupling the waveguide with an aqueous superstrate comprises placing the waveguide on the bottom plate of the flow cell, wetting the waveguide surface opposite the substrate with buffer solution to be used in measurements, and then placing the top plate with the attached prisms over the wetted waveguide. An advantage of the raised-channel waveguide structure is that effective prism coupling is easily accomplished by placing mild pressure on the coupling prisms.

Evanescent binding assays in two model systems were performed with the flow cell of FIGS. 4A, 4B, using a dual-channel assay format similar to that described by Herron et al. in "Fluorescent immunosensors using planar waveguides", *SPIE Vol.* 1885 (*Advances in Fluorescence Sensing Technology*), pp. 28-39, 1993, as well as in the copending U.S. patent application Ser. Nos. 08/064,608 and 08/263,522.

Example 4

Model Assays Using Thin-Film Waveguide Flow Cell

In the first or direct-binding model system, the binding of a biotinylated antibody labeled with a fluorescent tracer to avidin immobilized on the waveguide surface was measured. The particular antibody used was an anti-fluorescein antibody designated 9-40, produced by standard hybridoma methodology. The 9-40 antibody was labeled with the dye Cy-5 ($\lambda_{abs,max}$=650 nm, $\lambda_{em,max}$=667 nm, $e_{max}$=2×10$^5$ M$^{-1}$ cm$^{-1}$) according to the manufacturer's procedure (Biological Detection Systems). The labeling efficiency was approximately four dyes per protein molecule. An untreated hydrophilic SiON IOW surface was treated for 8 hr with a 0.2 mg/mL solution of avidin (obtained from Sigma) dissolved in phosphate-buffered saline (PBS, pH 7.4) to physically adsorb the avidin to the waveguide surface.

A portion of the Cy-5 labeled 9-40 was biotinylated using N-hydroxy-succinimidobiotin (Sigma). Specifically, a 20-fold molar excess of this reagent was added to a 1 mg/mL solution of 9-40 in 0.1 M sodium carbonate/sodium bicarbonate buffer, pH 9 (CBB). This mixture was allowed to react for 2 hr at room temperature, and the product (biotinylated, CY-5-conjugated 9-40) was purified by gel permeation chromatography using a PD-10 column (Pharmacia) equilibrated in PBS.

The second type of assay was an indirect, sandwich-type assay in which the binding of free fluorescein-conjugated BSA to immobilized anti-fluorescein antibody (antibody 9-40) was measured using an anti-BSA antibody conjugated with Cy-5 as a tracer. The IOW surfaces with immobilized 9-40 antibody were prepared as follows. Prior to immobilization, 9-40 was acid pre-treated in citrate buffer (pH 3) for 1 hr and reconstituted in PBS at a concentration of 2.3×10$^{-7}$ M (0.03 mg/ml), following the procedure described by Lin et al. (1989). SiON IOWs were treated with 1% dichlorodimethylsilane (DDS, Sigma), rinsed three times in deionized water, and then immersed in a solution of the acid-pretreated antibody 9-40 for 3 hr at room temperature.

Murine monoclonal anti-bovine serum albumin antibody (anti-BSA; available from Sigma) was labeled with Cy-5 as described for antibody 9-40. Bovine serum albumin (Sigma) was labeled with fluorescein isothiocyanate (FITC, Sigma). A 20-fold molar excess of FITC was added to a 1 mg/ml solution of BSA in CBB. This mixture was allowed to react for 1 hr at room temperature, and the conjugate was purified using a PD-10 column equilibrated in PBS. Labeling efficiency was approximately 2 FITC groups per BSA molecule. It should be noted that since the assays were performed with excitation at 632.8 nm, a wavelength which well exceeds the absorption band of FITC ($\lambda_{abs,max}$=492 nm), the FITC here serves solely as a hapten for 9-40, and not as a fluorescent tag.

Figure 5:
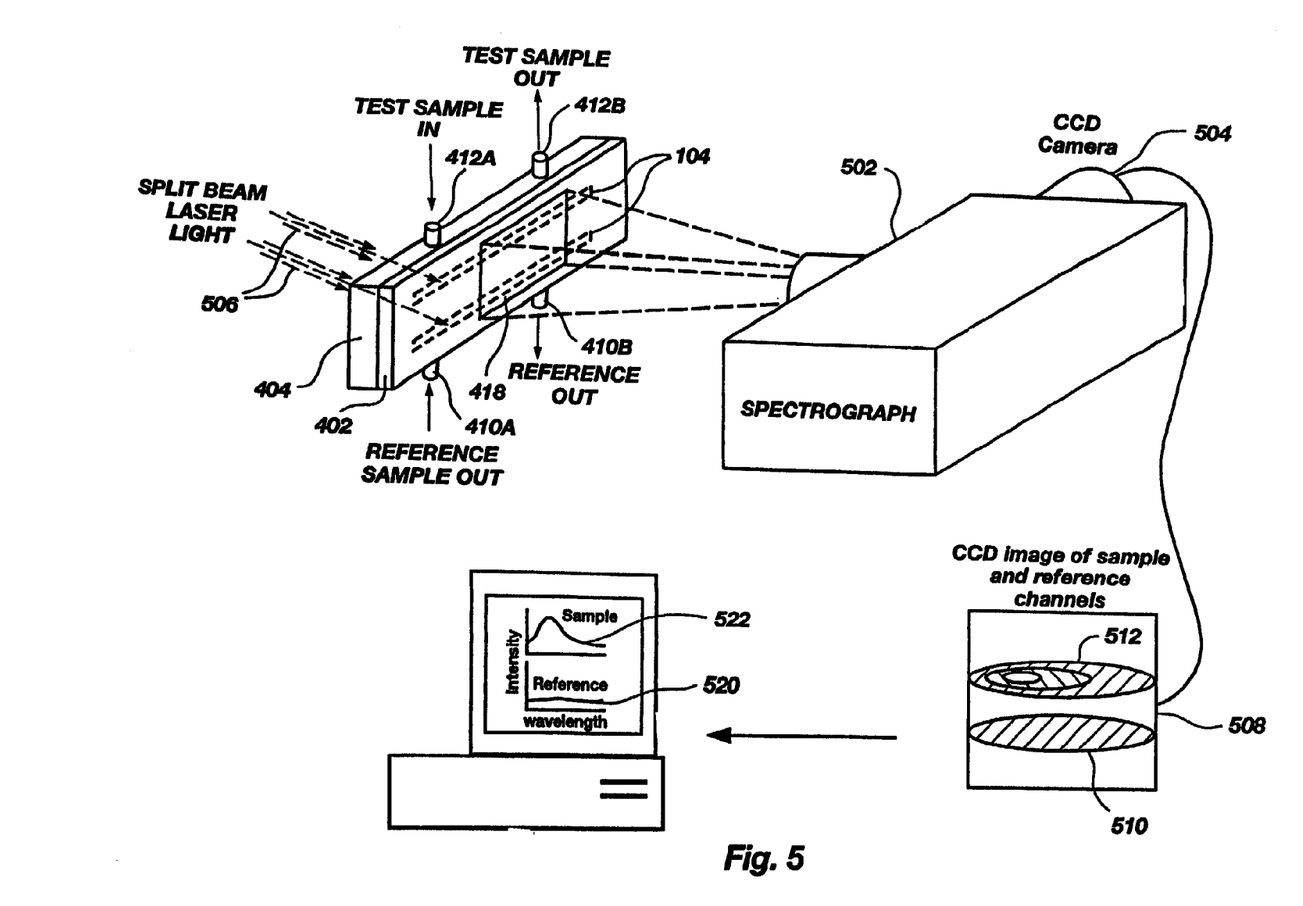
FIG. 5 is a schematic diagram of optical apparatus, including the flow cell of FIGS. 4A and 4B, for performing binding assays therewith.

To perform the assays, IOWs coated as described in the preceding paragraphs were mounted in a flow cell like that of FIG. 4A, and placed on a rotating goniometer (not shown) in the collection path of a spectrograph 502 associated with a CCD camera 504 (FIG. 5). The goniometer is optional but useful in an experimental set-up to ascertain the best coupling angle for coupling the laser beam into the waveguide. Once the best coupling angle has been determined and the apparatus standardized, a goniometer is not required to perform the assay. The input light was the red line (6 mW at 632.8 nm) of a HeNe laser (made by Melles Griot), split into dual beams 506 and simultaneously prism coupled into the two channels 408 of the composite waveguide. In this manner, a reference channel and a sample channel were excited.

For detection, the 1 mm wide guided modes in each channel were oriented perpendicular to the entrance slit of the spectrograph. Light emitted from a 1 mm long section of the two parallel streaks was imaged through the window 418 in the bottom plate 402 of the flow cell with a 50 mm f/5.6 camera lens onto the slit of spectrograph 502. The collected light emission was wavelength-dispersed using a single grating monochromator (SPEX 1681c Minimate-2, f/3.9, 300 grooves/mm) centered at 700 nm and directed onto a thermoelectrically cooled CCD camera 504 (Photometrics Series 200), producing an image 508 containing reference region 510 and sample region 512. The reference and sample image regions 510, 512 were separately binned and vertically integrated and converted on a MACINTOSH IIx computer to reference spectrum 520 and sample spectrum 522, respectively, of intensity vs. wavelength.

Both assays followed the same general scheme: 1) a capture protein was immobilized to the surface of both the sample and reference channels; 2) aliquots of the hapten-carrier protein conjugate (with fluorescent tracer) were added to the sample channel; and 3) the same concentration of fluorescent tracer (without hapten) was added simultaneously to the reference channel.

Each measurement began by collecting the baseline spectra of PBS buffer in both the sample and reference channels. Starting with the most dilute analyte solution, 1 mL of the sample and reference solutions described in Table 1 were injected into the flow cell. The solutions were incubated with the waveguide surface for 2 min for assay 1 and 5 min for assay 2, followed by collection of 10 sec spectrograph images of both channels. This process was repeated several times until the most concentrated solution was assayed. All CCD images were collected without a wash step, i.e., with the fluorescent analyte filling the sample and reference channel volume. Reference and sample spectra derived from each CCD image of each measurement were integrated from 653 nm to 693 nm. Binding curves were constructed from these data by taking the ratio of the integrated intensity of the sample to that of the reference, and then plotting these ratios as a function of bulk analyte concentration. Such ratiometric measurements compensated for two effects: nonspecific binding of the tracer and parasitic excitation of bulk fluorescence.

Figure 6A:
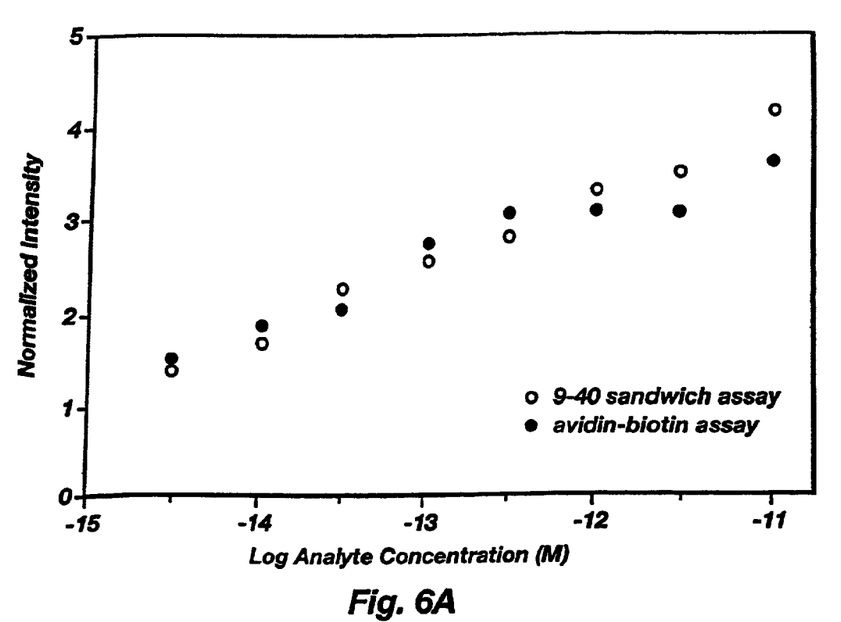
FIGS. 6A and 6B are charts of fluorescence measurements made with the apparatus of FIG. 4.
Figure 6B:
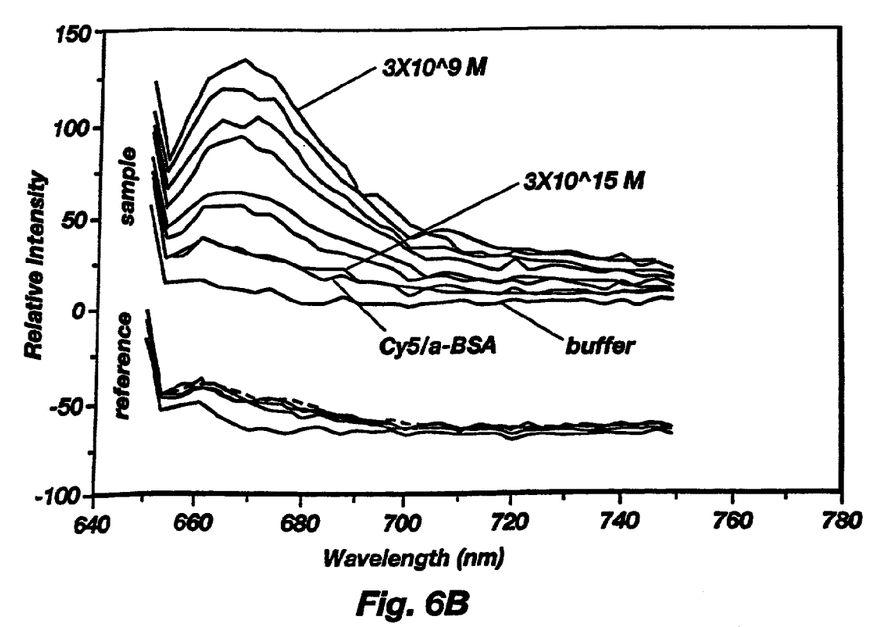

The results obtained with the two assay schemes are shown in FIGS. 6A-6B. The results indicate that analyte could be detected at concentrations as low as 3×10$^{-15}$ M with a two-channel Si$_2$O$_3$N thin-film waveguide flow cell. These measurements are at least 3.3×10$^4$ times more sensitive than the thin-film waveguide immunosensors reported by Sloper et al. or Zhou et al., op cit., and at least 33 times more sensitive than the thick-film sensor of Herron et al. 1993, op cit.

The prism coupling scheme described in Example 4 is efficient, simple, and well suited for use in laboratory experiments. However, such a device is relatively expensive and thus less than ideal for a disposable IOW module for use with a point-of-care optical unit. Further, the prism coupling scheme requires precise pressure on the prisms and precise alignment of the incident laser beam.

Figure 2A:
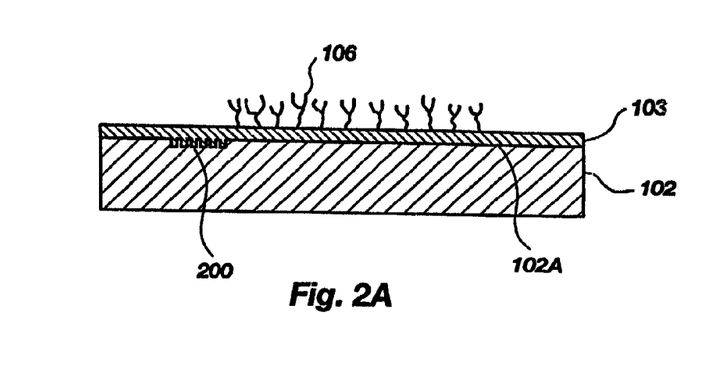
FIG. 2A is a side view of a composite waveguide having an integral etched grating coupler.

An alternate embodiment of a coupling scheme, which avoids these problems, is to provide a diffraction grating etched either into the surface of the waveguide opposite the substrate or into the substrate adjacent the waveguide. The presently preferred embodiment is that of a substrate-etched grating. As seen in FIG. 2A, the substrate 102 has a grating 200 etched into the surface 102A which is in contact with the thin-film waveguide 103. The binding molecules 106 are immobilized down-beam of the grating 200. Optionally, a second grating (not shown) may be etched into the substrate 102, down-beam of the immobilized binding molecules. Such a second grating is for purposes of optical characterization of the waveguide and is not required for purposes of the fluorescence binding assay.

The depicted substrate-etched grating is advantageous in that the light can be conveniently in-coupled from the back side of the device, and without interference from macromolecules bound to the waveguide surface. Also, it is convenient and economical from a manufacturing perspective to etch the grating into the substrate prior to deposition and etching of the channel waveguides.

Figure 2B:
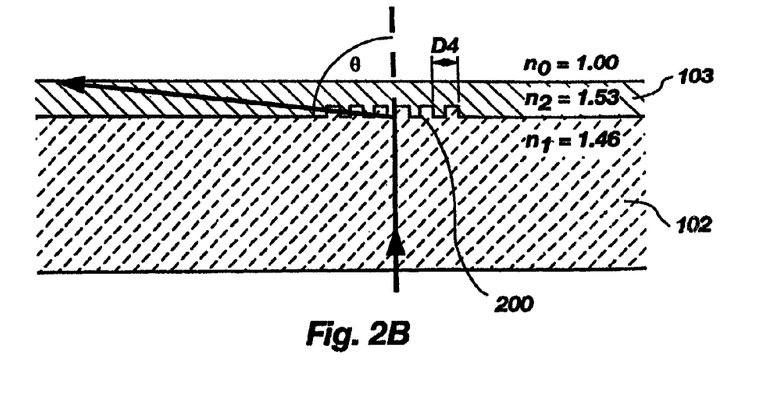
FIG. 2B is a schematic illustration of the embodiment of FIG. 2A showing diffraction of a normal incident light beam into a guided mode of the thin-film waveguide.

The efficiency of light incoupling by the etched grating will vary according to the spacing, the profile or blaze, and the aspect ratio of the grooves. These parameters should be optimized according to the wavelength of the input (excitation) light, the index of refraction of the superstrate, and the waveguide thickness by techniques conventional in the art. In the present case, a grating period $D_4$ of about 0.42 µm was computed for coupling of a normally incident 632.8 nm laser beam into the m=0 mode of the thin-film SiON waveguide ($\Theta$=83°; see FIG. 2B).

Figure 3A:
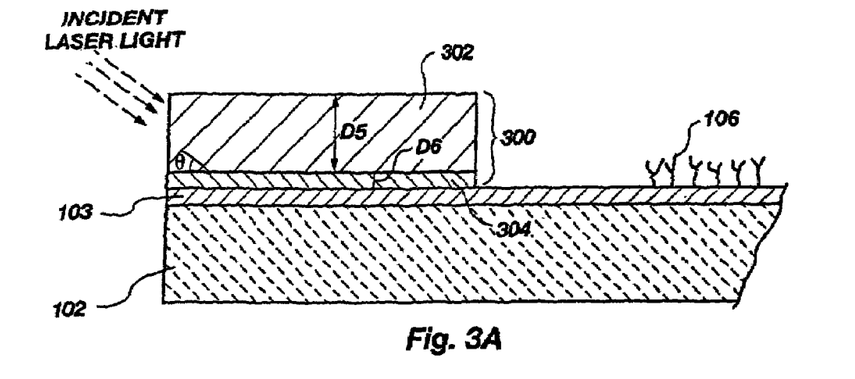
FIG. 3A is a side cross-sectional view of an alternate embodiment of a composite waveguide, having an integral waveguide coupler.
Figure 3B:
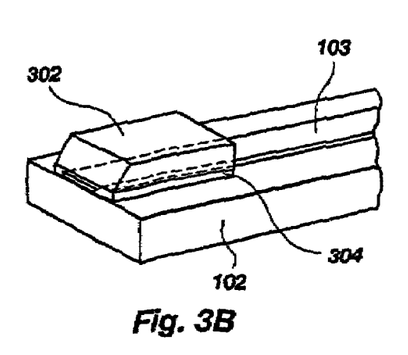
FIG. 3B is a perspective view of the embodiment of FIG. 3A.
Figure 3C:
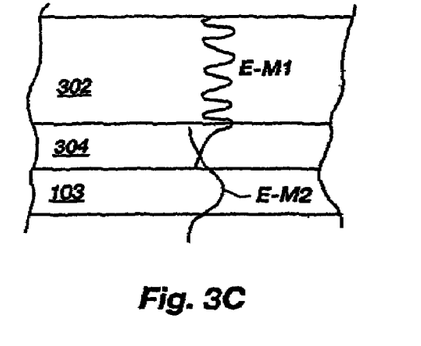
FIG. 3C is a schematic illustration of the overlap of the evanescent electromagnetic fields of the input waveguide and the thin-film waveguide.

Still another coupling scheme uses the principle of evanescent penetration to evanescently couple light from a waveguide coupler into the composite waveguide across a precise spacing layer (FIGS. 3A, 3B and 3C). The waveguide coupler is contactingly mounted on the upper surface of the composite waveguide, adjacent the exposed surface of the thin-film waveguide 103. Like the prism coupler, the waveguide coupler 300 does not extend into the region to which the specific binding molecules are immobilized.

As seen in FIG. 3A, the waveguide coupler 300 comprises an input waveguide 302 which consists of a comparatively thick (1 mm or greater) layer of material of refractive index $n_3$, and a thin spacing layer 304 of refractive index $n_4$, where $n_4$ is less than both $n_3$ and $n_2$. The input waveguide 302 has a receiving edge for receiving the input laser light and a thickness D5 which is sufficient to allow easy end coupling of the input beam into the receiving edge. The spacing layer 304 has a thickness D6 selected to maximize the evanescent coupling of waveguided light from the input waveguide 302 into the thin film of the composite waveguide.

According to coupled mode theory, light propagating in one waveguide can be synchronously coupled into an adjacent waveguide if there is overlap between the evanescent regions EM-1, EM-2 of the two waveguides in the low index region separating them (FIG. 3C). The efficiency of coupling depends upon the spacing between the guides, the respective modal propagation constants, and the distance of the interaction. Since the coupling efficiency varies according to the cosine of the distance of interaction, in theory, it will reach 100% at a certain length. Therefore, the synchronous evanescent coupling device should be quite efficient.

To achieve maximum coupling efficiency, the spacing layer thickness should be adjusted such that $K_1 = (j+1)\pi/2, (j=0,1,2\ldots)$ where K is the coupling constant and depends on the refractive indices $n_1$, $n_2$, $n_3$, $n_4$, the wavelength lambda of the input light, and the respective thicknesses D2, D5 and D6 of the thin-film waveguide 103, the input waveguide 302, and the spacing layer 304. With the thin-film waveguide 302, it should be taken into account that, generally, only one or a few of the lowest modes (preferably from j=0 to about j=10, and no more than j=20) are being propagated in the waveguide. Preferred waveguide couplers are configured to increase the proportion of laser light which is propagated in these lower modes.

For a silicon oxynitride composite waveguide, the spacing layer can be made of $SiO_2$. Desirably, the spacing layer 304 is deposited epitaxially, so that its thickness can be controlled very accurately at the time of deposition. The input waveguide 302 is attached on top of the spacing layer 304, after all epitaxial processing and etching steps have been finished in the fabrication of the composite waveguide. The input waveguide is made of a high refractive index material, such as rutile, zirconia, or a high-index glass, and may be adhered to the spacing layer 304 by an index-matching cement of refractive index near $n_3$. This assembly would be comparatively inexpensive, and is thus attractive for a disposable, one-time use module.

Preferably, as shown in FIG. 3A, the laser light is focussed into the receiving edge of the input waveguide at an angle $\Theta$ which is a degree or two less than the critical angle for TIR at the interface between the input waveguide and the spacing layer. Such angled beam entry has been found to substantially increase the proportion of internally propagated light in the evanescent tail, and thus the evanescent intensity.

Figure 7:
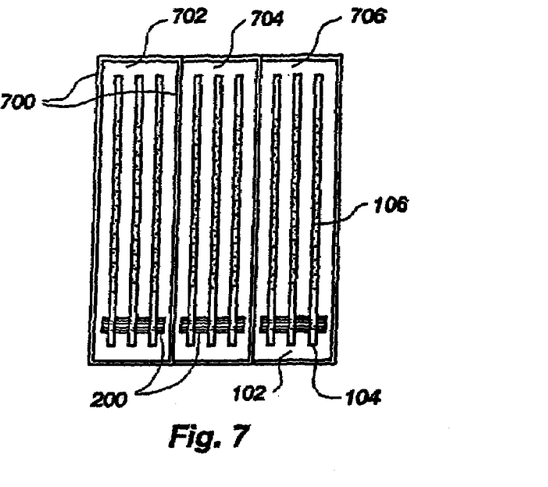
FIG. 7 is a top view of an alternate embodiment of a composite waveguide, having etched sample wells.

Still another embodiment is an IOW with integrally formed sample wells 702, 704, 706 (FIG. 7), each of which may contain multiple thin waveguide strips 104. In a preferred embodiment, walls 700 which enclose the wells are formed by layering a submicron cladding film of the substrate optical material on the composite waveguide, appropriately masking, and then etching the cladding back down to the SiON waveguide layer. These steps are performed prior to immobilization of the specific binding molecules. Sample wells thus constructed provide physically defined regions in which different antibodies can be immobilized, or to which different solutions, e.g., background or control samples vs. test samples, can be added. The same technique could be used to form open-ended longitudinal flow channels instead of the box-shaped reservoirs illustrated. Also, instead of layering the reservoir wall material over the composite waveguide, the same technique could be used to form reservoir or flow channel walls on a separate top plate.

At present, it is believed that two additional factors related to the chemistry of immobilization of specific binding molecules to the waveguide surface can affect the sensitivity achieved. These are 1) the relative amount of nonspecific protein binding to the thin-film surface (including the walls of any sample wells), and 2) the analyte/tracer-binding capacity of the immobilized binding molecules.

In a highly preferred embodiment of the multi-channel IOW, the IOW surface is treated to minimize nonspecific binding which otherwise can cause significant overlap of tracer signals between channels. The problem of such overlap worsens rapidly with increasing numbers of channels per IOW. Take as an example a six-channel waveguide divided into three adjacent-channel pairs in three corresponding separate wells, with anti-CK-MB immobilized to one member of each pair and anti-CK-NM immobilized to the other member. The IOW so constructed would permit simultaneous calibrated measurement of binding of 2 different analytes, CK-MB and CK-MM. If the level of nonspecific binding is assumed to be about 5% of the specific binding level, the channel with anti-CK-MB covalently attached will be contaminated to about 5% with nonspecifically adsorbed anti-CK-MM. Conversely, the channel with anti-CK-MM will be contaminated to about 5% with nonspecifically adsorbed anti-CK-MB. Thus, with such a 2-analyte IOW, there could be about 10% crosstalk between the channels, already an undesirable contribution to background level. For a 4-analyte IOW (twelve channels), however, the background contributed by such crosstalk would increase to about 30%, which would seriously impair detection sensitivity. Obviously, the problem worsens with increasing numbers of different analytes.

For this reason, it is highly desirable that the channels be coated with a coating that reduces nonspecific binding to 1% or less of specific binding, prior to covalent immobilization of the specific binding molecule.

A method of enhancing the number of available analyte binding sites is to site-specifically immobilize the analyte binding molecules. For antigen-binding fragments such as $F(ab')_2$'s, this can be accomplished by providing a base coating having pendant maleimido groups. The $F(ab')_2$ fragments are then reduced to yield Fab' fragments which contain a free thiol group at their C-terminal end, and this thiol group readily reacts to covalently couple the $F(ab')_2$ fragment to the maleimido group. Desirably, the coating with pendant maleimido groups also provides the inhibition of nonspecific binding discussed in the preceding paragraph; this may, for example, be accomplished by a base coating comprising chains of polymerized hydrophilic residues adhered via a silica-affinic moiety to the waveguide surface, as disclosed by the copending U.S. patent application Ser. No. 08/064,608 and 08/263,522. Protocols for achieving both of these methods can be found in the noted copending applications and in the literature in Herron et al., "Fluorescent immunosensors using planar waveguides", *SPIE* 1885:28-39, 1993. Preferably, at least 70% of the immobilized analyte binding molecules should be available for binding.

It will be apparent that details of the composite waveguide can be varied considerably without departing from the concept and scope of the invention. The claims alone define the scope of the invention as conceived and as described herein.

What is claimed is:

1. An apparatus for performing a specific binding assay, the apparatus comprising:
    a composite waveguide comprising:
        a substrate comprising a first optical material of refractive index $n_1$ and having a first planar surface and an opposite second surface, and
        a waveguide film comprising a second optical material having a refractive index $n_2$ which is greater than refractive index $n_1$, said waveguide film disposed on said first planar surface of said substrate;
    capture molecules, associated with said waveguide film, for interacting selectively with at least one type of selected analyte molecule;
    a light source operably disposed to direct a light beam into said composite waveguide for propagation by total internal reflection therein;
    a light detection device positioned to collect light emitted from a surface of said waveguide film; and
    an optical coupling element comprised of a waveguide coupler disposed on an upper surface of said waveguide film and opposite said first planar surface of said substrate, wherein said waveguide coupler is further comprised of an input waveguide that is comprised of an optical material having a refractive index $n_3$ and a thickness of between about 0.5 mm and about 5 mm and a precise spacing layer to evanescently couple light into said waveguide film across said precise spacing layer, said spacing layer comprises an optical material having a refractive index $n_4$, where $n_4 < n_2$ and $n_4 < n_3$.

2. The apparatus of claim 1, wherein said light detection device is positioned to detect light passing through said opposite second surface of said substrate of said composite waveguide.

3. The apparatus of claim 1, wherein said optical coupling element comprises at least one prism that focuses light into said waveguide film.

4. The apparatus of claim 1, wherein said optical coupling element comprises a diffraction grating that diffracts light into said waveguide film.

5. The apparatus of claim 4, wherein said diffraction grating is formed into said waveguide film at an upper surface thereof, opposite said first planar surface of said substrate.

6. The apparatus of claim 4, wherein said diffraction grating is formed into at least one of said first planar surface of said substrate and a surface of said waveguide film adjacent to said first planar surface.

7. The apparatus of claim 1, wherein said substrate has a thickness of at least about 10 μm.

8. The apparatus of claim 1, wherein said waveguide film has a thickness of at least about 0.1 μm.

9. The apparatus of claim 1, wherein said first optical material comprises at least one of silicon dioxide, quartz, fused silica, silicon oxynitride, and magnesium fluoride.

10. The apparatus of claim 1, wherein said second optical material comprises at least one of silicon oxynitride and silicon dioxide.

11. The apparatus of claim 1, wherein said light source comprises a laser.

12. The apparatus of claim 1, wherein said light detection device comprises a charge-coupled device.

13. The apparatus of claim 1, wherein said composite waveguide further comprises a sample reservoir configured to contain a sample solution adjacent to a surface of said waveguide film.

14. The apparatus of claim 13, wherein said sample reservoir contains a sample solution comprising a plurality of molecules of a selected analyte and a plurality of tracer molecules, said tracer molecules being activated by evanescent light escaping from said waveguide film into said sample solution.

15. The apparatus of claim 1, wherein said capture molecules are of a plurality of different types.

16. The apparatus of claim 15, wherein said different types of said capture molecules are positioned at discrete locations from one another on a surface of said waveguide film.

17. The apparatus of claim 16, wherein said discrete locations are arranged in an array.

18. The apparatus of claim 15, wherein said different types of capture molecules are capable of reacting with at least two different analytes.

19. The apparatus of claim 15, wherein said different types of capture molecules are capable of reacting with at least four different analytes.

20. An apparatus for performing a specific binding assay, the apparatus comprising:
    a composite waveguide comprising:
        a substrate comprising a first optical material of refractive index n, and having a first planar surface and an opposite second surface, and
        a waveguide film comprising a second optical material having a refractive index $n_2$ which is greater than refractive index n, said waveguide film disposed on said first planar surface of said substrate;
    capture molecules, associated with said waveguide film, for interacting selectively with at least one type of selected analyte molecule;

a light source operably disposed to direct a light beam into said composite waveguide for propagation by total internal reflection therein;

an optical coupling element comprising a waveguide coupler:
  disposed on an upper surface of said waveguide film, opposite said first planar surface of said substrate,
  that directs light into said waveguide film by evanescent coupling, and
  that includes an input waveguide and a spacing layer to evanescently couple light into said waveguide film across said spacing layer, the input waveguide comprising an optical material having a refractive index n, and a thickness of between about 0.5 mm and about 5 mm; and a light detection device positioned to collect light emitted from a surface of said waveguide film.

21. The apparatus of claim 20, wherein said light detection device is positioned to detect light passing through said opposite second surface of said substrate of said composite waveguide.

22. The apparatus of claim 20, wherein said optical coupling element comprises at least one prism that focuses light into said waveguide film.

23. The apparatus of claim 20, wherein said optical coupling element comprises a diffraction grating that diffracts light into said waveguide film.

24. The apparatus of claim 23, wherein said diffraction grating is formed into said waveguide film at an upper surface thereof, opposite said first planar surface of said substrate.

25. The apparatus of claim 23, wherein said diffraction grating is formed into at least one of said first planar surface of said substrate and a surface of said waveguide film adjacent to said first planar surface.

26. The apparatus of claim 20, wherein said spacing layer comprises an optical material having a refractive index $n_w$, where $n_4<n_1$ and $n_4<n_w$, said spacing layer having a thickness selected to optimize evanescent coupling of light from said input waveguide into said waveguide film.

27. The apparatus of claim 20, wherein said waveguide film has a thickness of at least about 0.1 μm.

28. The apparatus of claim 20, wherein said first optical material comprises at least one of silicon dioxide, quartz, fused silica, silicon oxynitride, and magnesium fluoride.

29. The apparatus of claim 20, wherein said second optical material comprises at least one of silicon oxynitride and silicon dioxide.

30. The apparatus of claim 20, wherein said light source comprises a laser.

31. The apparatus of claim 20, wherein said light detection device comprises a charge-coupled device.

32. The apparatus of claim 20, wherein said composite waveguide further comprises a sample reservoir configured to contain a sample solution adjacent to a surface of said waveguide film.

33. The apparatus of claim 32, wherein said sample reservoir contains a sample solution comprising a plurality of molecules of a selected analyte and a plurality of tracer molecules, said tracer molecules being activated by evanescent light escaping from said waveguide film into said sample solution.

34. The apparatus of claim 20, wherein said capture molecules are of a plurality of different types.

35. The apparatus of claim 34, wherein said different types of said capture molecules are positioned at discrete locations from one another on a surface of said waveguide film.

36. The apparatus of claim 35, wherein said discrete locations are arranged in an array.

37. The apparatus of claim 34, wherein said different types of capture molecules are capable of reacting with at least two different analytes.

38. The apparatus of claim 34, wherein said different types of capture molecules are capable of reacting with at least four different analytes.

39. An apparatus for performing a specific binding assay, the apparatus comprising:
  a composite waveguide comprising:
    a substrate comprising a first optical material of refractive index n, and having a first planar surface and an opposite second surface, and
    a waveguide film comprising a second optical material having a refractive index $n_2$ which is greater than refractive index $n_1$, said waveguide film disposed on said first planar surface of said substrate;
  capture molecules, associated with said waveguide film, for interacting selectively with at least one type of selected analyte molecule;
  a light source operably disposed to direct a light beam into said composite waveguide for propagation by total internal reflection therein;
  a light detection device positioned to collect light emitted from a surface of said waveguide film;
  a sample reservoir configured to contain a sample solution adjacent to a surface of said waveguide film; and
  an optical coupling element comprised of a waveguide coupler disposed on an upper surface of said waveguide film and opposite said first planar surface of said substrate, wherein said waveguide coupler is further comprised of an input waveguide that is comprised of an optical material having a refractive index $n_3$ and a thickness of between about 0.5 mm and about 5 mm and a precise spacing layer to evanescently couple light into said waveguide film across said precise spacing layer, said spacing layer comprises an optical material having a refractive index $n_4$, where $n_4<n_2$ and $n_4<n_3$.

40. The apparatus of claim 39, wherein said light detection device is positioned to detect light passing through said opposite second surface of said substrate of said composite waveguide.

41. The apparatus of claim 39, wherein said optical coupling element comprises at least one prism that focuses light into said waveguide film.

42. The apparatus of claim 39, wherein said optical coupling element comprises a diffraction grating that diffracts light into said waveguide film.

43. The apparatus of claim 42, wherein said diffraction grating is formed into said waveguide film at an upper surface thereof, opposite said first planar surface of said substrate.

44. The apparatus of claim 42, wherein said diffraction grating is formed into at least one of said first planar surface of said substrate and a surface of said waveguide film adjacent to said first planar surface.

45. The apparatus of claim 39, wherein said waveguide film has a thickness of at least about 0.1 μm.

46. The apparatus of claim 39, wherein said first optical material comprises at least one of silicon dioxide, quartz, fused silica, silicon oxynitride, and magnesium fluoride.

47. The apparatus of claim 39, wherein said second optical material comprises at least one of silicon oxynitride and silicon dioxide.

48. The apparatus of claim 39, wherein said light source comprises a laser.

49. The apparatus of claim 39, wherein said light detection device comprises a charge-coupled device.

50. The apparatus of claim 39, wherein said capture molecules are of a plurality of different types.

51. The apparatus of claim 50, wherein said different types of said capture molecules are positioned at discrete locations from one another on a surface of said waveguide film.

52. The apparatus of claim 51, wherein said discrete locations are arranged in an array.

53. The apparatus of claim 50, wherein said different types of capture molecules are capable of reacting with at least two different analytes.

54. The apparatus of claim 50, wherein said different types of capture molecules are capable of reacting with at least four different analytes.

55. An apparatus for performing a specific binding assay, the apparatus comprising:
   a composite waveguide comprising:
      a substrate comprising a first optical material of refractive index n, and having a first planar surface and an opposite second surface, and
      a waveguide film comprising a second optical material having a refractive index $n_2$ which is greater than refractive index $n_1$, said waveguide film disposed on said first planar surface of said substrate;
   a plurality of different types of capture molecules associated with said waveguide film, each type of capture molecules configured to interact selectively with at least one type of selected analyte molecule, different types of capture molecules of said plurality positioned at discrete locations from one another and arranged in an array on a surface of said waveguide film;
   a light source operably disposed to direct a light beam into said composite waveguide for propagation by total internal reflection therein;
   a light detection device positioned to collect light emitted from a surface of said waveguide film; and
   an optical coupling element comprised of a waveguide coupler disposed on an upper surface of said waveguide film and opposite said first planar surface of said substrate, wherein said waveguide coupler is further comprised of an input waveguide that is comprised of an optical material having a refractive index $n_3$ and a thickness of between about 0.5 mm and about 5 mm and a precise spacing layer to evanescently couple light into said waveguide film across said precise spacing layer, said spacing layer comprises an optical material having a refractive index $n_4$, where $n_4<n_2$ and $n_4<n_3$.

56. The apparatus of claim 55, wherein said light detection device is positioned to detect light passing through said opposite second surface of said substrate of said composite waveguide.

57. The apparatus of claim 55, wherein said optical coupling element comprises at least one prism that focuses light into said waveguide film.

58. The apparatus of claim 55, wherein said optical coupling element comprises a diffraction grating that diffracts light into said waveguide film.

59. The apparatus of claim 58, wherein said diffraction grating is formed into said waveguide film at an upper surface thereof, opposite said first planar surface of said substrate.

60. The apparatus of claim 58, wherein said diffraction grating is formed into at least one of said first planar surface of said substrate and a surface of said waveguide film adjacent to said first planar surface.

61. The apparatus of claim 55, wherein said waveguide film has a thickness of at least about 0.1 μm.

62. The apparatus of claim 55, wherein said first optical material comprises at least one of silicon dioxide, quartz, fused silica, silicon oxynitride, and magnesium fluoride.

63. The apparatus of claim 55, wherein said second optical material comprises at least one of silicon oxynitride and silicon dioxide.

64. The apparatus of claim 55, wherein said light source comprises a laser.

65. The apparatus of claim 55, wherein said light detection device comprises a charge-coupled device.

* * * * *